(12) United States Patent
Lee et al.

(10) Patent No.: US 8,101,135 B2
(45) Date of Patent: Jan. 24, 2012

(54) DESKTOP STERILIZER FOR BOOKS

(75) Inventors: Jong Min Lee, Seongnam-si (KR); Sang Ok Woo, Guri-si (KR); Gun Hee Han, Seoul-si (KR)

(73) Assignee: IVS, Inc., Seoul-si (KR)

( * ) Notice: Subject to any disclaimer, the term of this patent is extended or adjusted under 35 U.S.C. 154(b) by 430 days.

(21) Appl. No.: 12/472,828

(22) Filed: May 27, 2009

(65) Prior Publication Data

US 2009/0317309 A1 Dec. 24, 2009

(30) Foreign Application Priority Data

Jun. 20, 2008 (KR) .............................. 2008-0058097

(51) Int. Cl.
*A61L 2/00* (2006.01)
*A61L 9/00* (2006.01)
(52) U.S. Cl. .............. 422/300; 422/292; 422/5; 422/22; 422/24
(58) Field of Classification Search .................. 422/292, 422/295, 300, 306, 22, 24, 28, 5
See application file for complete search history.

(56) References Cited

FOREIGN PATENT DOCUMENTS

| JP | 2001187121 A | * | 7/2001 |
|---|---|---|---|
| JP | 2001-336877 | | 12/2001 |
| JP | 2005185302 A | * | 7/2005 |
| KR | 10-0416317 | | 1/2004 |

OTHER PUBLICATIONS

English translation of JP 2001-187121 A.*
English translation of JP 2001-336877 A.*
English rranslation of JP 2005-185302 A.*

* cited by examiner

*Primary Examiner* — Sean E Conley
*Assistant Examiner* — Regina M Yoo
(74) *Attorney, Agent, or Firm* — Michael J. Striker

(57) ABSTRACT

The present invention provides a desktop sterilizer for books. The sterilizer includes an openable main body which has a sterilization chamber therein and is closable by a door so as to be openable through an opening, and a book holder which is provided in the sterilization chamber to maintain the covers of a book in a state of being unfolded. The sterilizer further includes a sterilizing UV lamp which sterilizes the book, and an air discharger which is connected to a blower and blows air towards the proximal edges of pages bound to a book spine of the book held by the book holder, thus opening the pages of the book. The sterilizer further includes a static electricity generating unit which charges the book with static electricity, such that the pages of the book are laid open by a static electric repulsive force, an aroma generating unit which generates an aroma and supplies it into the sterilization chamber using the air discharger, and a control computer which controls the sterilizing UV lamp and the blower.

5 Claims, 6 Drawing Sheets

DESKTOP STERILIZER FOR BOOKS

BACKGROUND OF THE INVENTION

1. Field of the Invention

The present invention relates generally to desktop sterilizers for books and, more particularly, to a desktop sterilizer for books which is installed in a library, a book rental store, a kindergarten, etc. such that an administrator or a user can easily and effectively sterilize books which are used by an unspecified number of the general public.

2. Description of the Related Art

Generally, various books which are rent, read or otherwise used by an unspecified number of the general public may be contaminated by different users, food or the like, thus resulting in the propagation of mold or germs. Therefore, the users may be exposed to various diseases attributable to contact having been made with such books.

Particularly, in the case where the pages of a book which are in the overlapped state and which are also covered with covers are contaminated, even should the book be sterilized by a typical ultraviolet (UV) sterilizer, the effect of sterilizing the book is not satisfactory, because UV rays cannot irradiate the interior, that is, the pages of the book.

Representative conventional techniques pertaining to sterilizers were proposed in Korean Patent Registration No. 0416317 or Japanese Patent Laid-open Publication No. 2001-336877.

The technique proposed in No. 0416317 pertains to a sterilizer for shoes which is constructed such that an auxiliary UV lamp is inserted into a shoe to sterilize it. Thus, this technique cannot be used to sterilize books having many pages.

In the book dryer proposed in No. 2001-336877, a blower dries pages of a book while it is being sterilized by a sterilization lamp. However, in this technique, hot air passes through the book in the direction parallel to the spine of the book. Here, when hot air passes between the pages of the book, air pressure between the pages becomes lower than that of the outside of the pages in accordance with Bernoulli's theorem. Thereby, the pages are in close proximity to each other, so that UV rays cannot effectively radiate the pages of the book.

Furthermore, the pages of a book may not be completely laid open by just placing the book in a rectangular chamber such that the book spine is disposed at the lower position. For example, in the cases of a thin and small book, such as a poetry collection, a novel having soft covers (many books stored in a library have soft covers), or a children's story book having a small number of pages each of which is thick, this technique cannot be used.

The inventor of the present invention inquired into the conventional problems assiduously and found out the following facts. If UV rays can be irradiated onto the book in a state in which covers and pages of the book are completely laid open, a satisfactory sterilization effect of preventing contagion by various diseases attributable to contact with contaminated books can be obtained. Furthermore, in a library or the like, if in addition to an administrator of books users can also easily sterilize the books using a book sterilizer, the users can be educated such that they more voluntarily and more often use the book sterilizer. As a result, the users can be protected from contagion by various diseases attributable to contact being made with contaminated books, and the books can be managed such that they are prevented from being contaminated from contaminants, thus extending the lifetime of the books, thereby reducing costs for the repurchase of books which are frequently used. The inventor developed the present invention on the basis of these facts.

SUMMARY OF THE INVENTION

Accordingly, the present invention has been made keeping in mind the above problems occurring in the prior art, and an object of the present invention is to provide a desktop sterilizer for books in which covers of a book and several tens or hundreds of sheets of pages can be evenly laid open by an air discharger and a static electricity generating unit such that sterilization using UV rays and chemical sterilization using an aroma generating unit can be effectively conducted, thus exhibiting a satisfactory sterilization effect of preventing contagion by various diseases attributable to contact being made with contaminated books.

Another object of the present invention is to provide a desktop sterilizer for books which is constructed such that when the book is sterilized by UV rays, hot air is supplied to the book, thus maximizing the effect of sterilizing the book using UV rays.

A further object of the present invention is to provide a desktop sterilizer for books in which means for maintaining the covers and pages of the book in the open state is provided on a movable table which is provided so as to be retractable into and out of a sterilization chamber, so that even a large or heavy book can be easily processed in the sterilizer.

In order to accomplish the above object, the present invention provides a desktop sterilizer for books, including: an openable main body having a sterilization chamber defined by top and bottom surfaces, a rear wall and sidewalls, the main body being closable by a door 10 so as to be openable through an opening; a book holder provided in the sterilization chamber to maintain the covers of a book in a state of being unfolded; at least one sterilizing UV lamp provided in the sterilization chamber to sterilize the book, the covers of which are held by the book holder; at least one air discharger connected to a blower and provided in the sterilization chamber at a position facing the book holder, the air discharger blowing air towards the proximal edges of pages bound to a book spine of the book held by the book holder, thus opening the pages of the book, and preventing the pages from remaining in close proximity to each other due to Bernoulli's theorem; a static electricity generating unit charging the book with static electricity, such that the pages of the book are laid open by static electric repulsive force; an aroma generating unit generating an aroma and supplying it into the sterilization chamber using the air discharger to fumigate the book using the aroma, thus chemically sterilizing the book using the anti-virus and anti-bacterial effects of the aroma; and a control computer controlling the sterilizing UV lamp and the blower, the control computer being connected to a control panel provided on the main body.

Preferably, the book holder and the air discharger may be provided on the bottom surface of the sterilization chamber.

Alternatively, the book holder and the air discharger may be provided on a movable table which is provided in the sterilization chamber so as to be retractable into and out of the sterilization chamber through the opening of the openable main body.

The book holder may include a book support and clamping members which hold the covers of the book such that they are maintained in the unfolded state.

Preferably, an electric heater may be provided on the blower, such that hot air is supplied to the book through the air discharger.

Furthermore, a transparent window may be provided in the door of the openable main body.

The desktop sterilizer may further include an operating state display provided on the front surface of the openable main body. The operating state display is connected to the control computer.

The desktop sterilizer may further include a page holding unit, having: at least one semi-circular setting rib, with protrusions being provided on the semi-circular setting rib at positions spaced apart from each other at regular intervals, the protrusions extending predetermined lengths downwards from the semi-circular setting rib to maintain the pages of the book in the open state; and extensions respectively extending outwards from both ends of the semi-circular setting rib, the extensions being inserted into the book support so as to be movable upwards or downwards.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, the present invention will be described in detail with reference to the attached drawings.

Figure 1:
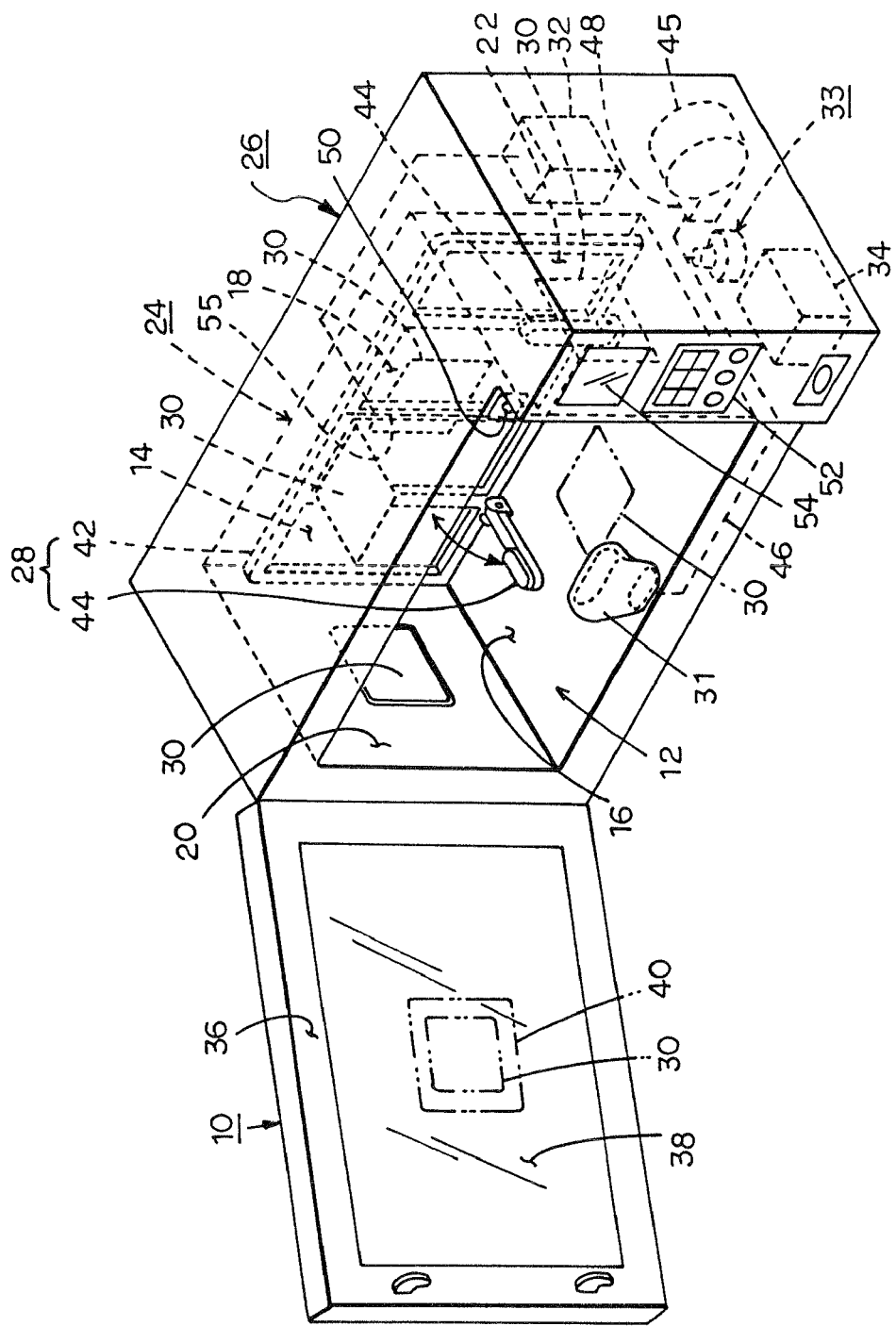
FIG. 1 is a perspective view illustrating a desktop sterilizer for books, according to a first embodiment of the present invention.
Figure 2:
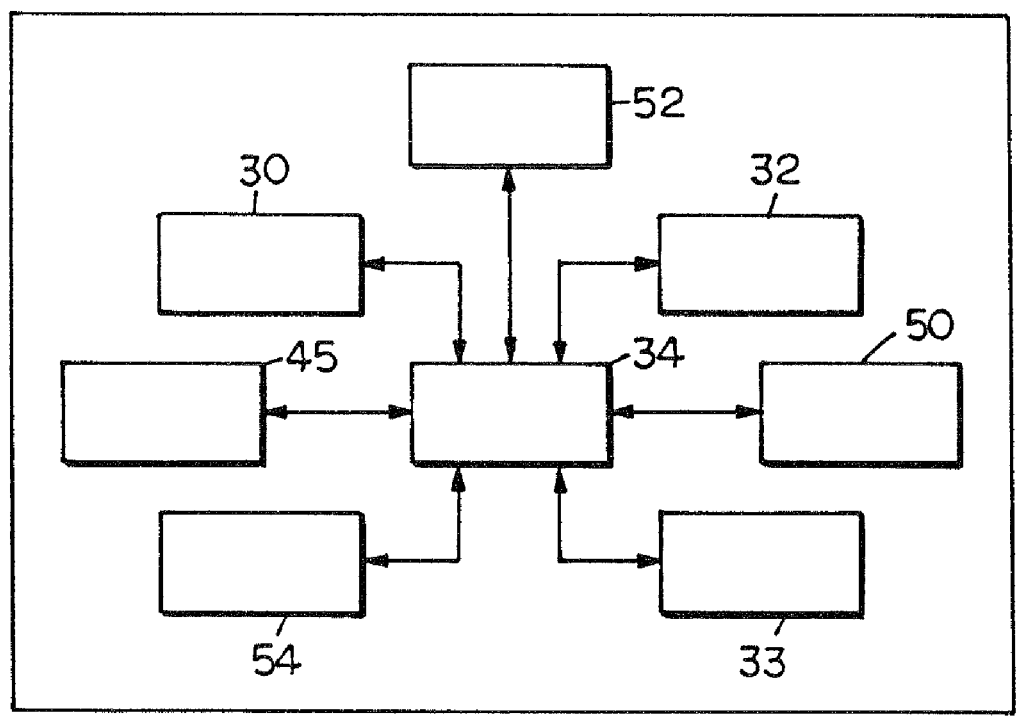
FIG. 2 is a schematic diagram showing the construction of the desktop sterilizer according to the present invention.
Figure 3:
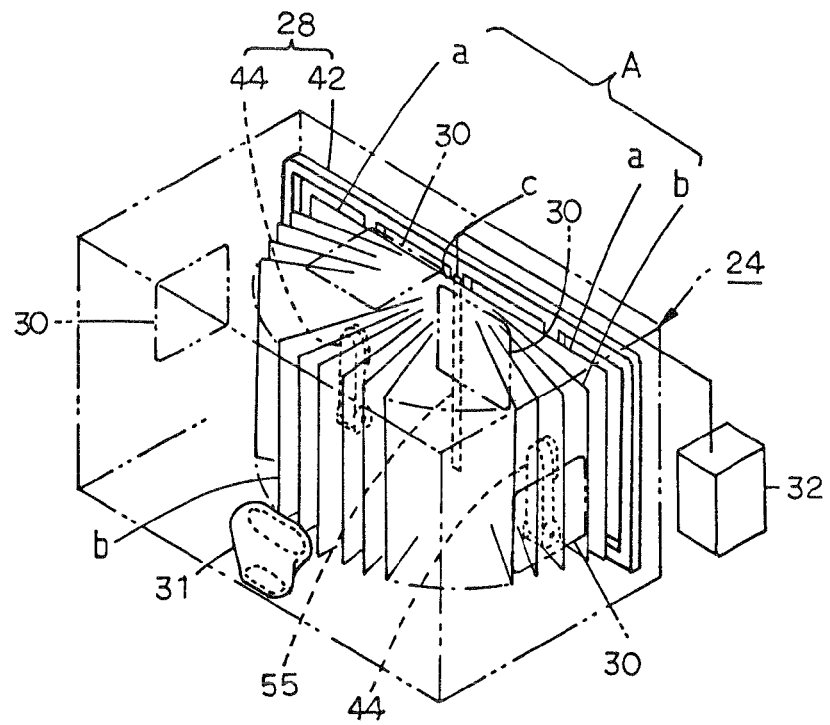
FIG. 3 is a perspective view showing the use of the desktop sterilizer of FIG. 1.
Figure 4:
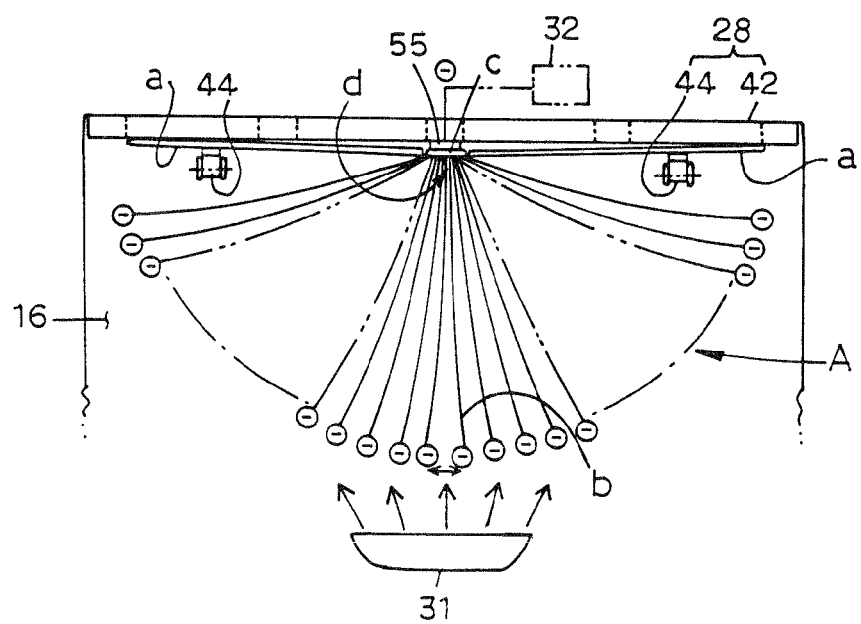
FIG. 4 is a plan view showing the use of the desktop sterilizer of FIG. 1.
Figure 5:
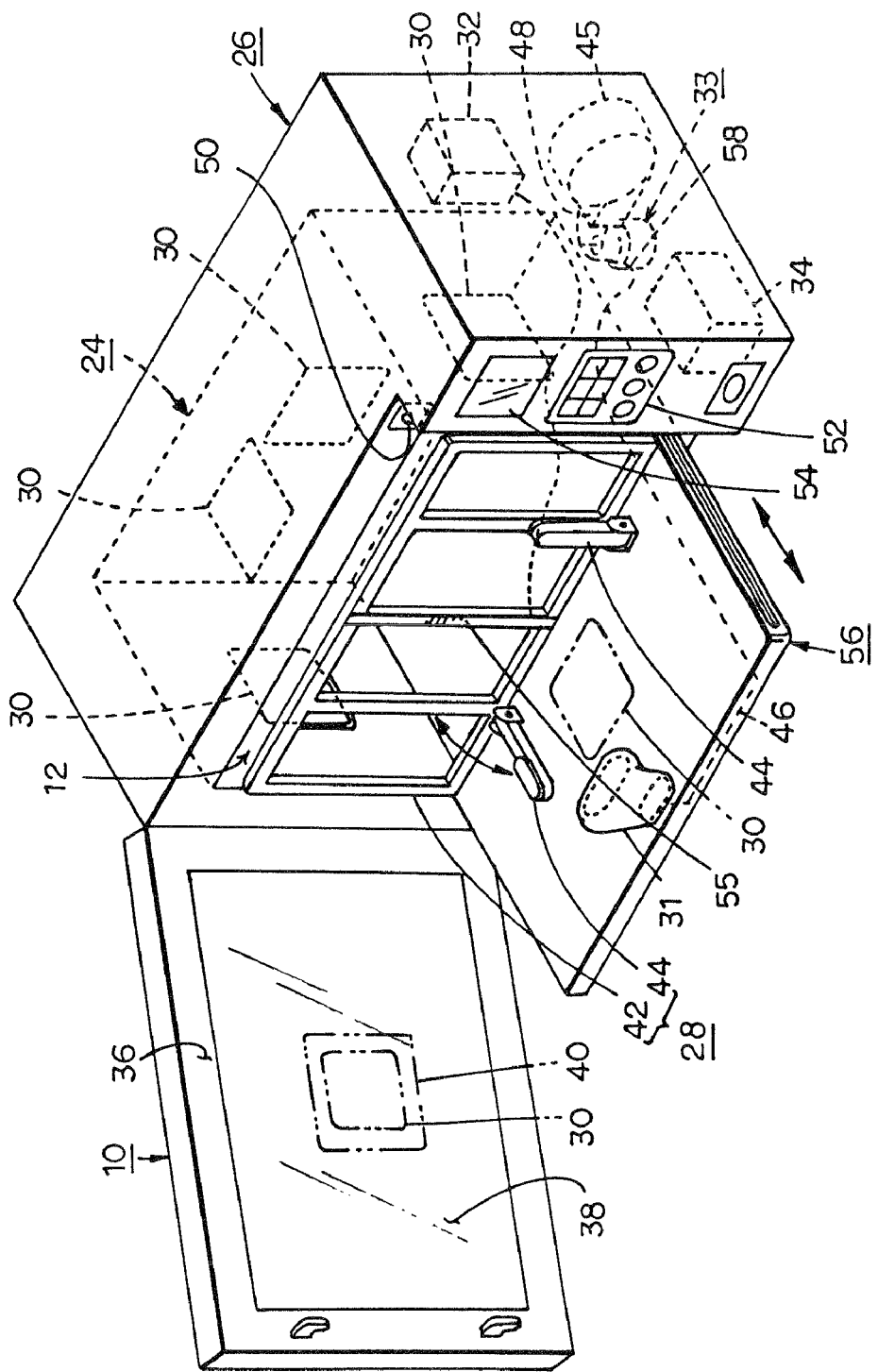
FIG. 5 is a perspective view illustrating a desktop sterilizer for books, according to a second embodiment of the present invention.
Figure 6:
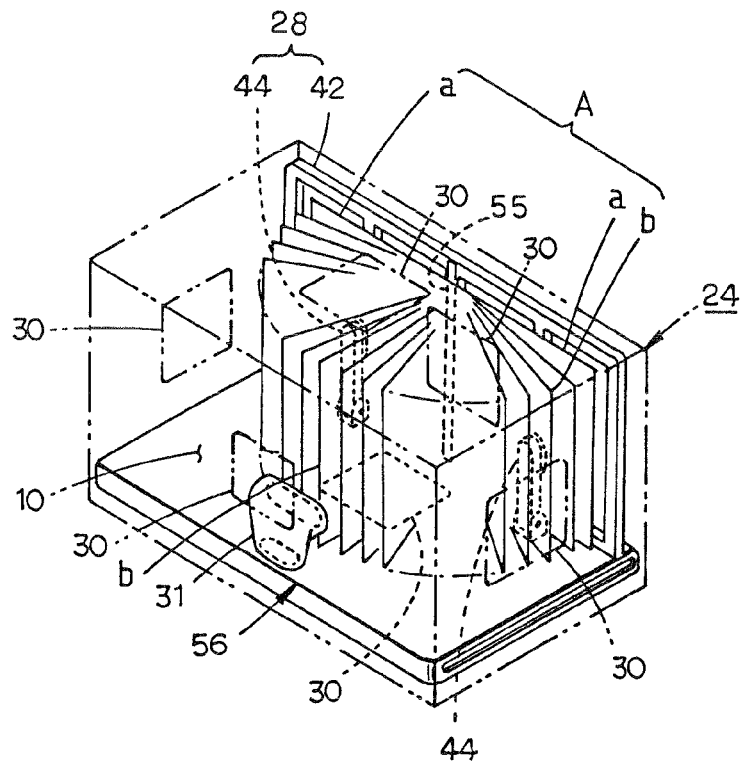
FIG. 6 is a perspective view showing the use of the desktop sterilizer of FIG. 5.
Figure 7:
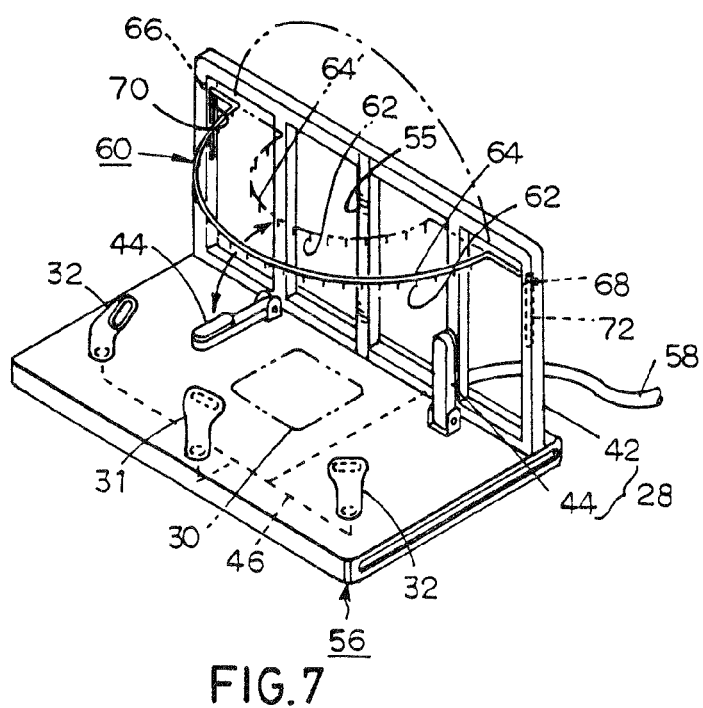
FIG. 7 is a perspective view illustrating a desktop sterilizer for books, according to a third embodiment of the present invention.
Figure 8:
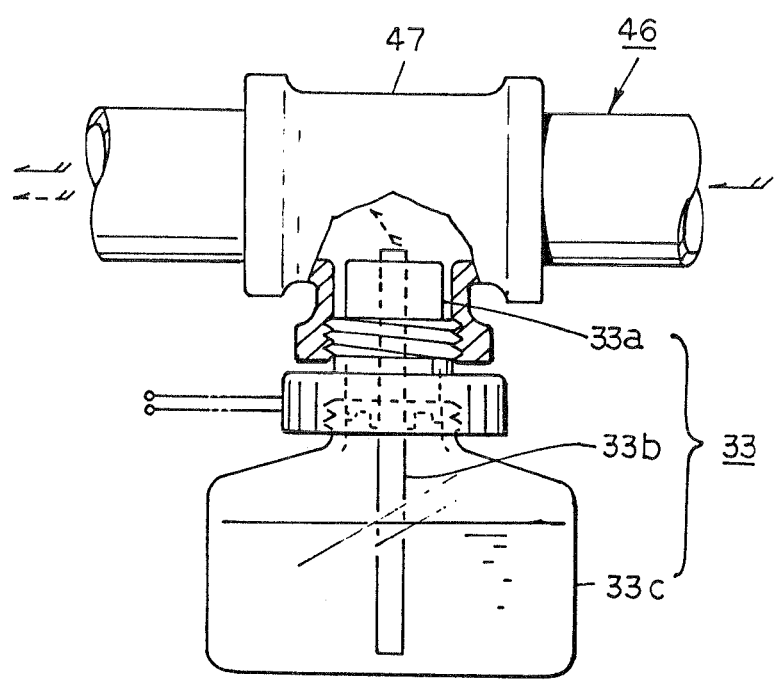
FIG. 8 is a view illustrating an aroma generating unit of FIG. 1.
Figure 9:
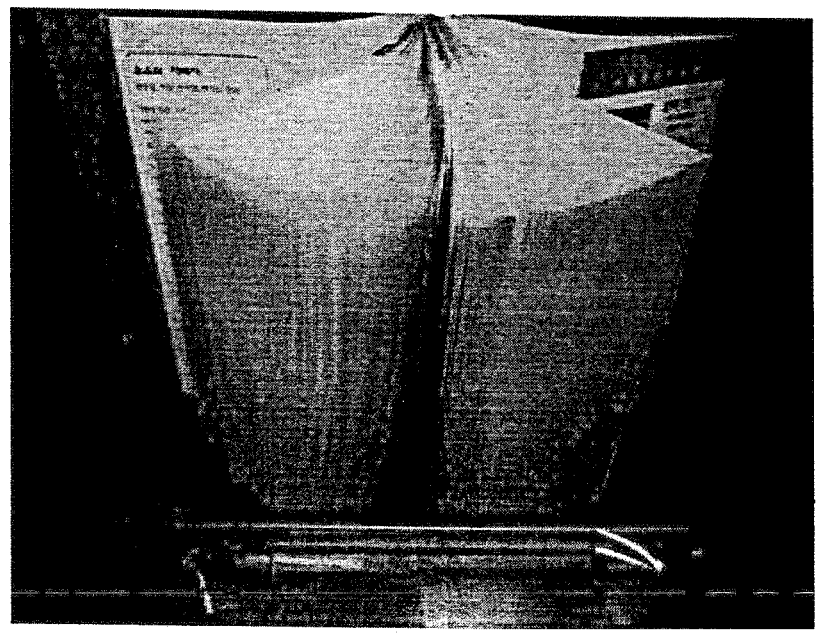

FIG. 1 is a perspective view illustrating a desktop sterilizer for books, according to a first embodiment of the present invention. FIG. 2 is a schematic diagram showing the construction of the desktop sterilizer according to the present invention. FIG. 3 is a perspective view showing the use of the desktop sterilizer of FIG. 1. FIG. 4 is a plan view showing the use of the desktop sterilizer of FIG. 1. FIG. 5 is a perspective view illustrating a desktop sterilizer for books, according to a second embodiment of the present invention. FIG. 6 is a perspective view showing the use of the desktop sterilizer of FIG. 5. FIG. 7 is a perspective view illustrating a desktop sterilizer for books, according to a third embodiment of the present invention. FIG. 8 is a view illustrating an aroma generating unit of FIG. 1.

As shown in FIGS. 1 and 3, the desktop sterilizer of the present invention includes an openable main body 26, a book holder 28, at least one sterilizing ultraviolet (UV) lamp 30, at least one air discharger 31, a static electricity generating unit 32, at least one aroma generating unit 33, and a control computer 34.

The openable main body 26 has a sterilization chamber 24 which is defined by top and bottom surfaces 14 and 16, a rear wall 18 and sidewalls 20 and 22 and is closable by a door 10 so as to be openable through an opening 12.

The book holder 28 is provided in the sterilization chamber 24 and holds covers (a) of a book A to be sterilized to maintain the book A in a state of being unfolded.

The at least one sterilizing UV lamp 30 is provided in the sterilization chamber 24 to sterilize the book A, the covers (a) of which are held by the book holder 28.

The at least one air discharger 31 is provided in the sterilization chamber 24 at a position facing the book holder 28. The air discharger 31 blows air towards the proximal edges of pages (b) bound to a book spine (c) of the book A, the covers (a) of which are held by the book holder 28, thus opening the pages (b) such that UV rays emitted from the sterilizing UV lamp 30 can be evenly radiated onto all of the pages (b) of the book A.

The static electricity generating unit 32 is provided on the book holder 28 and charges the book A that is held by the book holder 28 with static electricity, so that the pages (b) of the polarized book A are laid open by static electric repulsive force.

The at least one aroma generating unit 33 is provided on an air supply pipe 46, through which air is supplied from the air discharger 31 to the book A. The aroma generating unit 33 generates aroma and supplies it into the sterilization chamber 24 using the air discharger 31 to fumigate the book using the aroma, thus chemically sterilizing the book A using the anti-virus and anti-bacterial effects of the aroma.

The control computer 34 controls the operation of the sterilizing UV lamp 30, the air discharger 31, the static electricity generating unit 32 and the aroma generating unit 33.

Referring to FIG. 1, the door 10 includes a frame 36, and a transparent window 38 which is supported by the frame 36 and is made of a transparent glass or acryl plate to allow a user to easily observe a sterilization state of the book A placed in the sterilization chamber 24 without opening the door 10.

The sterilizing UV lamp 30 may comprise a plurality of sterilizing UV lamps 30. In this case, as shown in FIG. 1, the sterilizing UV lamps 30 are respectively provided on the top surface 14, the rear wall 18 and the sidewalls 20 and 22 which form the sterilization chamber 24. Thus, in the state in which the covers (a) of the book A are unfolded and held by the book holder 28, the sterilizing UV lamps 30 sterilize the entire book A, the pages (b) of which are laid open by the air discharger 31. In order to increase a range within which UV rays are directly radiated onto the book A, as shown by the double-dotted and dashed line of FIG. 1, an ultraviolet isolation plate 40, along with the sterilizing UV lamp 30, may be provided on the bottom surface 16 of the sterilization chamber 24 or on the transparent window 38 of the door 10.

As shown in FIGS. 1 and 3, the book holder 28 includes a book support 42 which is placed upright on the rear portion of the bottom surface 16 of the openable main body 26, and a pair of clamping members 44 which are pivoted at the lower ends thereof to the bottom surface 16, such that the upper ends of the clamping members 44 are rotatable towards the book support 42 or the bottom surface 16. Therefore, when sterilizing the book A, the book holder 28 holds the book A such that the book A is placed upright and the covers (a) thereof are maintained in the state of being unfolded at 180°.

Preferably, as illustrated in FIG. 1, to prevent the book support 42 from blocking UV rays emitted from the sterilizing UV lamp 30 that is disposed on the rear wall 18 of the sterilization chamber 24, the book support 42 has, for example, a lattice structure which is partially open.

The air discharger 31 is connected to a blower 45 which absorbs air and supplies it to the air discharger 31 in an electric operating manner through the air supply pipe 46. As shown in FIGS. 3 and 4, the air discharger 31 discharges air towards the proximal edges of the pages (b) bound to the book spine (c) of the book, thus preventing the conventional problem in which the pages (b) remain in close proximity to each other in accordance with the Bernoulli's theorem. Therefore, the pages (b) of the book A can be evenly exposed.

The blower 45 includes an electric heater 48 which generates hot air. Thus, hot air discharged through the air discharger 31 further enhances the sterilization effect of the sterilization UV lamps 30 and effectively eliminates moisture which causes the propagation of mold or germs.

The sterilization UV lamps 30 and the blower 45 are connected to the control computer 34, and they are also connected to a door opening sensing switch 50 which is provided around the opening 12 of the main body 26 at a position corresponding to the door 10, so that they are operated in conjunction with the opening or closing of the door 10. Therefore, when the door 10 is in the closed state, the sterilization UV lamps 30 and the blower 45 can be operated to sterilize and dry the book A placed in the sterilization chamber 24. When a user opens the door 10 to put the book A into the sterilization chamber 24 or remove it therefrom, the operation of the sterilization UV lamps 30 and the blower 45 is stopped, thus ensuring the safety of the user. As such, the sterilization UV lamps 30 and the blower 45 can be efficiently controlled.

Furthermore, an operating state display 54 and a control panel 52 which is connected to the control computer 34 are provided on the front surface of the main body 26, so that the user can easily control and observe the operation of the book sterilizer of the present invention.

As shown in FIGS. 1, 2 and 4, a static electricity charging plate 55 is connected to the static electricity generating unit 32 and is vertically provided on the central portion of the book support 42. In the state in which the covers (a) of the book A are unfolded and placed upright by the book support 42 and the clamping members 44, the static electricity charging plate 55 charges the pages (b) with electricity through the book spine (c) of the book A such that the pages (b) have the same polarity (−). Thereby, as shown in FIG. 4, the pages (b) of the book A can be smoothly opened not only by air discharged from the air discharger 31 but also by the static electric repulsive force.

Therefore, UV rays emitted from the sterilization UV lamps 30 and air which contains aroma generated from the aroma generating unit 33 and is supplied into the sterilization chamber 24 through the air discharger 31 can reach the proximal edges (d) of the pages (b) of the hook A, thus maximizing the effect of sterilizing the book A.

As shown I FIG. 1, the aroma generating unit 33 is provided on the air supply pipe 46 which connects the air discharger 31 to the blower 45.

For example, as shown in FIG. 8, the aroma generating unit 33 includes an electric heating fumigator 33a which is coupled to a T-shaped connector 47 provided on the air supply pipe 46, and an aroma cartridge 33c which is coupled to the electric heating fumigator 33a and has a wick 33b.

Meanwhile, the sterilizer for books according to the second embodiment of the present invention is illustrated in FIGS. 5 and 6.

In the book sterilizer according to the second embodiment shown in FIGS. 5 and 6, a book holder 28 and the air discharger 31 are provided on a movable table 56 which is placed in a sterilization chamber 24 so as to be retractable into and out of the sterilization chamber 24 through an opening 12 of a main body 26. In this case, a large or heavy book can also be easily processed by the book sterilizer. Furthermore, other than having a structure in which a flexible air supply hose 58 is connected between the air discharger 31 and a blower 45 because a distance therebetween is variable, the general construction of the book sterilizer of the second embodiment remains the same as that of the first embodiment of FIGS. 1 through 3.

FIG. 7 illustrates the desktop sterilizer for books according to the third embodiment of the present invention. The book sterilizer of FIG. 7 further includes a page holding unit 60 which is provided on a book support 42 of a book holder 28 to set the pages (b) of the book A in a state of being laid open.

The page holding unit 60 includes at least one semi-circular setting rib 64. Protrusions 62 extend predetermined lengths downwards from the setting rib 64 and are spaced apart from each other at regular intervals. In addition, extensions 66 and 68 respectively extend outwards from both ends of the setting rib 64 in opposite directions. The extensions 66 and 68 are respectively inserted into slots 70 and 72 which are formed in both ends of the book support 42, such that the page holding unit 60 is compatible with various books having different heights.

Furthermore, as shown by the solid line and double-dotted and dashed line of FIG. 7, a small semi-circular setting rib 64' may be provided along with the semi-circular setting rib 64 such that the page holding unit 60 is also compatible with various books having different widths.

In addition, the air discharger 31 may be constructed such that it can be rotated or reciprocated to the left and right by a drive unit (not shown) having a typical structure. Alternatively, as shown in FIG. 7, a plurality of air dischargers 31 may be provided.

The book sterilizer of the present invention having the above-mentioned construction is placed on a table for lending/reading in a library, a book rental store, a kindergarten, etc. such that an administrator or a user can easily use the book sterilizer. For example, the user can easily sterilize a book to be read before or after using the book.

As described above, the present invention provides a desktop sterilizer for books which can easily sterilize books rent, read or otherwise used by an unspecified number of the general public. In the desktop sterilizer of the present invention, air containing an aroma is blown towards a book and static electricity is applied to the pages of the book such that the pages are completely laid open by blown air and static electric repulsive force. In this state, UV rays and aroma are applied not only to the covers of the book but also the entire surface area of each of the pages, thus reliably sterilizing the entire book. Therefore, the present invention can guide users such that a user more voluntarily and more often uses the book sterilizer to preserve his/her own and his/her family's health from germs or mold that are present in the book. As a result, the users can be protected from contagion by a variety of diseases attributable to making contact with contaminated books.

Furthermore, the books can be managed such that they are prevented from being contaminated by contaminants, thus extending the lifetime of the books, thereby reducing costs for repurchasing books which are frequently used.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A desktop sterilizer for sterilizing a book using a sterilizing lamp while pages of the book are laid open by blowing air towards the book, comprising:
    an openable main body having a sterilization chamber defined by top and bottom surfaces, a rear wall and sidewalls, the sterilization chamber being closable by a door so as to be openable through an opening;
    a book holder supporting the book such that the book is placed upright and covers of the book are maintained in an unfolded state, the book holder comprising a book support placed upright on a rear portion of the bottom surface of the openable main body, and a pair of clamping members pivoted at lower ends thereof to the bottom surface so as to be rotatable towards the book support or the bottom surface;
    an air discharger connected to a blower through an air supply pipe and disposed in the sterilization chamber at a position facing the book support of the book holder, the air discharger blowing air towards proximal edges of the pages bound to a book spine of the book supported by the book support;
    a static electricity generating unit including a static electricity charging plate vertically provided on a central portion of the book support, the static electricity charging plate charging the pages of the book supported by the book holder with one polarity of static electricity;
    an aroma generating unit provided on the air supply pipe, the aroma generating unit generating an aroma to fumigate the book using the aroma, wherein the aroma is supplied into the sterilization chamber through the air discharger; and
    a control computer to control the air discharger, the static electricity generating unit and the aroma generating unit, the control computer being connected to a control panel provided on the openable main body.

2. The desktop sterilizer as set forth in claim 1, further comprising:
    a movable table provided in the sterilization chamber so as to be retractable into and out of the sterilization chamber through the opening of the openable main body, wherein the book holder and the air discharger are provided on the movable table.

3. The desktop sterilizer as set forth in claim 1, wherein a transparent window is provided in the door of the openable main body.

4. The desktop sterilizer as set forth in claim 1, further comprising:
    an operating state display provided on a front surface of the openable main body, the operating state display being connected to the control computer.

5. The desktop sterilizer as set forth in claim 1, further comprising:
    a page holding unit, comprising: at least one semi-circular setting rib, with protrusions being provided on the semi-circular setting rib at positions spaced apart from each other at regular intervals, the protrusions extending predetermined lengths downwards from the semi-circular setting rib to maintain the pages of the book in the laid open state; and extensions respectively extending outwards from both ends of the semi-circular setting rib, the extensions being inserted into the book support so as to be movable upwards or downwards.

* * * * *